United States Patent [19]

Baines et al.

[11] Patent Number: 5,855,898
[45] Date of Patent: Jan. 5, 1999

[54] THICKENER FOR COSMETIC COMPOSITION

[75] Inventors: Pamela E. Baines, Warrington; Peter W. Stanier, Sandbach, both of United Kingdom

[73] Assignee: Crosfield Limited, Warrington, England

[21] Appl. No.: 756,903

[22] Filed: Dec. 2, 1996

[30] Foreign Application Priority Data

Dec. 1, 1995 [GB] United Kingdom ............... 9524575

[51] Int. Cl.$^6$ ...................................................... A61K 7/00
[52] U.S. Cl. ........................ 424/401; 424/96.3; 424/78.03
[58] Field of Search .................. 424/401, 96.3, 424/78.03

[56] References Cited

U.S. PATENT DOCUMENTS

| 5,420,106 | 5/1995 | Parab | 514/2 |
| 5,422,112 | 6/1995 | Williams | 424/401 |
| 5,545,402 | 8/1996 | Watkinson | 424/94.63 |

FOREIGN PATENT DOCUMENTS

| 2 555 443 | 5/1985 | France | A61K 7/15 |
| 195 09 434 A1 | 9/1995 | Germany | A61K 7/02 |
| WO 88/04921 | 7/1988 | WIPO | A61K 7/15 |
| WO 95/03811 | 2/1995 | WIPO | A61K 31/74 |
| WO 96/17050 | 6/1996 | WIPO | C11D 3/50 |

*Primary Examiner*—Thurman K. Page
*Assistant Examiner*—D. Faulkner
*Attorney, Agent, or Firm*—Pillsbury Madison & Sutro LLP

[57] ABSTRACT

A thickening system containing an amorphous silica and xanthan gum in a silica/xanthan gum weight ratio from 160:1 to 2:1, preferably 100:1 to 5:1, most preferably 30:1 to 6.5:1 can be used to stabilise and thicken cosmetic compositions containing alpha-hydroxy carboxylic acids.

12 Claims, No Drawings

THICKENER FOR COSMETIC COMPOSITION

FIELD OF THE INVENTION

The present invention relates to an improved thickener for low pH cosmetic compositions, particularly those in lotion or cream form. The present invention also relates to a thickened cosmetic composition.

BACKGROUND

Aqueous cosmetic compositions often require thickeners to give them an aesthetically pleasing viscosity. Also for a cosmetic to be effective, it is desirable to be substantive to the skin. Thickeners provide this substantivity. Furthermore, even though the products may be effective to the consumer, ineffectiveness can be indicated if the system has watery consistency i.e. low viscosity. Products of watery consistency are also aesthetically displeasing to consumers with expectations of rich and creamy products.

Formulators of cosmetic compositions are increasingly recognising the numerous benefits that alpha-hydroxy acids have to offer. The reported benefits attainable from the use of alpha-hydroxy acids include a tighter skin-feel and emollient action, giving the skin a softer and smoother aspect and also a healthier and more even-looking complexion with a useful and visible reduction of facial lines.

Some cosmetic formulations are extremely difficult to thicken and even when initially thickened may have storage stability problems. Low pH systems such as cosmetic formulations containing alpha-hydroxy acids (AHA in the rest of the description) are particularly sensitive and difficult.

Currently, thickeners used for low pH systems are limited to Magnesium Aluminium Silicate (obtainable from R. T. Vanderbilt Company Inc. under the trade name Veegum), Xanthan gum (obtainable from Kelco International under the trade name Keltrol 1000), Hydroxyethylcellulose (obtainable from Aqualon BV under the trade name Natrosol 250HHR) and Polyacrylamide.

Cosmetic compositions containing AHAs and above mentioned thickeners are for example disclosed in W095/03811 or W094/27574. These materials deliver a degree of rheological control in low pH formulations, but are not ideal. The problems with these materials include:

(i) Poor viscosity control of magnesium aluminium silicate at low pH.

(ii) A stringy/tacky characteristic of the cellulose.

(iii) A definite "gummy" feel on the skin during rub out of the xanthan and cellulose.

(iv) A degree of unpredictability relating to the procedure for addition of the polyacrylamide to the formulation.

There is therefore a need for a thickener which is easily dispersed in the water phase of the formulation; is unaffected by high processing temperatures (75°–800° C.); is unaffected by acidic pH (3 to 5) and more importantly yields a thixotropic formulation. In addition, the final cosmetic formulation must deliver a "rich and creamy" skin-feel, which is easily absorbed into the stratum corneum and leaves little or no after-feel.

It is therefore a goal of the present invention to develop a thickening system which is effective at low pH and also stabilises oil and water emulsions to prevent syneresis. It is also a goal of the present invention to develop cosmetic compositions, which are stable at high temperatures.

It is a further goal of the present invention to develop a cosmetic composition containing AHA which delivers a "rich and creamy" skin-feel, is easily absorbed into the stratum corneum and leaves little or no after-feel.

It has now been found that a system comprising an amorphous silica and xanthan gum can be particularly effective.

Definitions, Tests and Procedures i. Nitrogen surface area—pore volume

Nitrogen surface area is determined by standard nitrogen adsorption methods of Brunauer, Emmett and Teller (BET) using a multi point method with an ASAP 2400 apparatus supplied by Micromeritics of the U.S.A.. The samples are outgassed under vacuum at 270° C. for at least one hour before measurement. Surface area is calculated from the volume of nitrogen gas adsorbed at p/po 0.98. This apparatus also provides the pore size distribution from which it is possible to get the pore size ($D_{10}$) for which 10% of the pores are below this pore size. In the same manner, it is possible to get the pore size for which 50% ($D_{50}$) and 90% ($D_{90}$) of the pores are below this pore size. Additionally the pore volume ($cm^3/g$) for a given range of pore size can be obtained from the desorption curve. It is therefore possible to obtain the percentage of the pore volume contained in pores having a diameter between 10 and 30 nanometers.

ii. Rheology Analysis

Creams and lotions are generally viscoelastic materials possessing a yield point and shear thinning behaviour. The yield value of a material is defined as the stress required to shear or deform the material. Hence, a dynamic stress rheometer was used to determine the linear viscoelastic region, which is a measure of the inherent strength of the structure of the emulsion.

The Theological properties were measured using a Dynamic Stress Rheometer supplied by Rheometrics Inc. Epsom, England. Parallel plates were used having a diameter of 40 mm and a gap set at 0.542 mm with an auto-calibrated tool inertia value of 367.5 $g/cm^2$. A dynamic stress sweep test was used to determine the dynamic viscoelastic properties of the AHA compositions at 25° C. The dynamic stress sweep test increased linearly from 0 to 500 Pa at a frequency of 0.1 rad $s^{-1}$ and increments of 50. A 60 second delay was employed prior to test to ensure consistency of sample application.

A 3D graph of storage or elastic modulus (G'), loss or viscous modulus (G") and viscosity was plotted against shear stress, for all compositions to determine the products' flow characteristics.

The shear stress contribution by gravity is approximately 20 Pa (Bell, 1988), therefore products with yield points below this will flow readily by themselves and hence appear runny. A lotion or cream with a yield value above 20 Pa will flow more slowly, giving the impression of 'body'. However a product which retains its elasticity (G') at high stresses can be perceived as stringy/too viscous.

iii. Weight mean particle size

The weight mean particle size is determined with the aid of a Malvern Mastersizer using 45 mm path length lens. This instrument, made by Malvern Instruments, Worcestershire uses the principle of Mie scattering, utilising a low power He/Ne laser. Before measurement the sample was dispersed ultrasonically in water for a period of 7 minutes to form an aqueous suspension. The Malvern Mastersizer measures the weight particle size distribution of the silica. The weight mean particle size ($d_{50}$), the 10 percentile ($d_{10}$) and the 90 percentile ($d_{90}$) are easily obtained from the data generated by the instrument.

iv. CTAB surface area

This method determines the specific surface area of samples, exclusive of area contained in micropores too small to admit hexadecyltrimethyl ammonium bromide (cetyltrimethyl ammonium bromide, commonly referred to as CTAB) molecules.

The isotherm for adsorption of an aqueous solution of CTAB at a charged surface has a long horizontal plateau corresponding to a bilayer coverage of the substrate surface. Rapid equilibration is achieved by using mechanical agitation. Titration with sodium dodecyl sulphate solution is used to determine the unadsorbed CTAB after removal of the dispersed silica by centrifugation.

Into a 50 cm$^3$ screw-cap jar weight between 0.10 and 0.25 g of silica, depending upon surface area to be determined. For high surface areas, which lead to low CTAB titrations, the lower weight is employed. Add 25 cm$^3$ of 0.01 mol.dm$^{-3}$ CTAB solution and bring the pH of the mixture to 9.0 with 0.1 mol.dm$^{-3}$ NaOH solution. Stopper the jar and agitate for 1 hour in a water bath set at 25° C. Settle the suspension centrifugally and transfer 5 cm$^3$ of the supernatant into a 50 cm$^3$ measuring cylinder. Add 10 cm$^3$ of deionised water, 15 cm$^3$ of chloroform, 10 cm$^3$ of mixed indicator solution (dimidium bromide/disulphine blue obtainable from BDH Ltd, Poole, Dorset, England) and titrate with 0.005 mol.dm$^{-3}$ sodium dodecyl sulphate solution, previously calibrated by a standard CTAB solution. The titration end point is that point at which the chloroform layer becomes pale-pink. Record the volume of sodium dodecyl sulphate to reach the end point as $V_2$ cm$^3$. Conduct a blank titration in a similar manner on 5 cm$^3$ of the stock CTAB solution and record the volume of sodium dodecyl sulphate as $V_1$ cm$^3$.

Calculate the CTAB surface per gram of silica by the following equation in which the calculation is based on a molecular cross section of the bromide of 35 Å$^2$:

$$CTAB \text{ surface area} = \frac{(V_1 - V_2) \times 5.27}{W} \times (0.5)$$

Where W=Weight of silica sample (in grams) 0.5 accounts for bi-layer formation.

General Description of the Invention

It is a first objective of the present invention to provide a cosmetic composition comprising:
i) from about 0.01 to 20% by weight, preferably 0.1 to 10%, most preferably 3 to 8%, of $C_1$–$C_{25}$ alpha-hydroxy carboxylic acids and their salts and mixtures thereof;
ii) from about 0.05 to 0.5% by weight, preferably 0.1 to 0.3% of xanthan gum;
iii) from about 0.5 to 8% by weight, preferably 1 to 5%, most preferably 2 to 4%, of an amorphous silica;
v) a cosmetically acceptable carrier.

Preferably, in the cosmetic composition according according to the present invention, amorphous silica and xanthan gum are present in a silica/xanthan gum weight ratio from 160:1 to 2:1, preferably 100:1 to 5:1, most preferably 30:1 to 6.5:1.

Preferably the cosmetic composition has a pH of between 3 and 5.

Preferably also, the amorphous silica is at least in part an amorphous silica having a pore size distribution wherein 90% of the pores have a diameter above 15 nanometers, and less than 20% of the pore volume is in pores having a pore diameter between 10 and 30 nanometers, the amorphous silica having a CTAB surface area of less than 100 m$^2$/g. Preferably, the particle size distribution of the silica is such that the $d_{50}$ is comprised between 1.0 μm and 8.0 μm, most preferably between 3.0 μm and 6.0 μm. Most preferably the amorphous silica is a silica as described in WO 94/11302. Another preferred amorphous silica is fumed silica.

It is a second objective of the present invention to provide a cosmetic composition comprising;
i) from about 0.01 to 20% by weight, preferably 0.1 to 10%, most preferably 3 to 8.0%, of $C_1$–$C_{25}$ alpha-hydroxy carboxylic acids and their salts and mixtures thereof,
ii) a cosmetically acceptable carrier,
iii) less than 0.5% by weight, preferably less than 0.1% by weight, of magnesium aluminium silicate, this cosmetic composition having a viscosity range from about 2,000 Pa s$^-$ to 80,000 Pa s$^{-1}$, preferably 4,000 Pa s$^{-1}$ to 45,000 Pa s$^{-1}$, most preferably 8,000 Pa s$^{-1}$ to 30,000 Pa s$^{-1}$.

Preferably the cosmetic composition has a pH of between 3 and 5.

DETAILED DESCRIPTION OF THE INVENTION

The present invention will be further illustrated with reference to the following examples.

Example 1

Control Cream

A 5% Glycolic acid cream was prepared based on a formulation and procedure presented by R.T. Vanderbilt in the 'Bath and Body Formulary' section of Cosmetics and Toiletries Vol 110, April 1995, page 83.

As with most low pH cosmetic compositions, Veegum was used as the thickener/rheological additive and was referenced as the Control. The Control (referred to as C1 in the following description) was formulated with 1.4% Veegum Ultra, 0.3% xanthan gum and 0.7% triethanolamine. A cream having the following composition by weight was thus produced:

| A. | Deionised Water | 63.45(%) |
|---|---|---|
| B. | Thickening system | |
|  | Veegum Ultra (1) | 1.40(%) |
|  | Keltrol 1000 (2) | 0.30(%) |
|  | Triethanolamine | 0.70(%) |
| C. | Other ingredients | |
|  | Glycerin | 4.80(%) |
|  | Crodacol C90EP | 2.90(%) |
|  | Arlacel 165 | 4.30(%) |
|  | Pristerene 4900 | 1.40(%) |
|  | Estol 1517 | 4.30(%) |
|  | Fancol FAO | 4.30(%) |
|  | DC200/350 | 1.40(%) |
|  | Glycolic acid | 7.15(%) |
|  | Sodium hydroxide (50%) | 2.70(%) |
|  | Germal II | 0.90(%) |

(1) Veegum Ultra is Magnesium Alumino Silicate obtainable from R. T. Vanderbilt Company Inc.
(2) Ketrol 1000 is a xanthan gum obtainable from Kelco International The pH of this composition was 3.5.

Comparative Example 2

The amorphous silica used in Example 2 was Sipernat D10 available from Degussa.

A cosmetic composition was produced to be compared with the Control (see Example 1) in which the thickening system was changed but all the other ingredients (except deionised water) were kept identical to those used in Example 1, the weight balance being reached by adjusting the amount of deionised water.

It was discovered that silica-only formulations demonstrated syneresis at high temperatures, therefore xanthan gum was added in minimum amounts to the silica formulations since the binder promoted storage stability. Triethanolamine was not required for silica based compositions.

This composition had the following formulation.

|    | Deionised water (%) by weight | Keltrol 1000(%) by weight | silica (%) by weight | Other (%) by weight |
|----|-------------------------------|---------------------------|----------------------|---------------------|
| C2 | 63.75                         | 0.1                       | 2.0                  | 34.15               |

The pH of this composition was 3.5.

Examples 3–5 of the Invention

For these examples a silica was used which was prepared according to patent WO 94/11302 in which the particle size distribution was: $d_{10}$ 1.1 µm, $d_{50}$ 4.4 µm and $d_{90}$ 9.2 µm.

In order to compare the performance of silicas as thickening agents, formulations were prepared in which the silicas were included between 2 to 3%.

Three cosmetic compositions were produced to be compared with the Control (see Example 1) in which the thickening system was changed but all the other ingredients (except deionised water) were kept identical to those used in Example 1, the weight balance being reached by adjusting the amount of deionised water. Xanthan gum was added in minimum amounts to bind the formulations containing silica, and also to give enhanced storage stability. Triethanolamine was not required for silica based compositions.

These 3 compositions had the following formulations.

|    | Deionised water (%) by weight | Keltrol 1000(%) by weight | silica (%) by weight | Other (%) by weight |
|----|-------------------------------|---------------------------|----------------------|---------------------|
| C3 | 63.65                         | 0.2                       | 2.0                  | 34.15               |
| C4 | 63.55                         | 0.3                       | 2.0                  | 34.15               |
| C5 | 62.75                         | 0.1                       | 3.0                  | 34.15               |

Example 6 of the invention

The silica used in example 6 was Aerosil 200, a fumed silica available from Degussa.

A cosmetic composition was prepared to be compared with the control (see Example 1) in which the thickening system was changed but all the other ingredients (except deionised water) were kept identical to those used in Example 1, the weight balance being reached by adjusting the amount of deionised water. Xanthan gum was added to bind the formulation containing silica and also to give enhanced storage stability. Triethanolamine was not required for silica based compositions as it was used as a buffer for Veegum and was therefore eliminated.

This composition had the following formulation.

|    | Deionised water (%) by weight | Keltrol 1000(%) by weight | silica (%) by weight | Other (%) by weight |
|----|-------------------------------|---------------------------|----------------------|---------------------|
| C6 | 63.65                         | 0.2                       | 2.0                  | 34.15               |

The rheology profile of each composition, plus the Control, was assessed after 1 day and at 2 weeks and 1 month intervals thereafter. The creams were subjected to rigorous stability tests, including 1 month storage at 45° C and 4° C., five freeze/thaw cycles and periodical room temperature monitoring.

Formulation integrity was preserved under all these conditions, but only the 45° C. stability results are presented as this is the most demanding test. The results for rheology and stability analysis are summarized in Table 1. The rheology profile of each composition at 1 day, 2 weeks and 1 month intervals is referenced 1, 2 and 3 respectively in these tables. "Y" represents composition stability with no visual separation, whereas "N" represents composition instability with visual separation.

|    | Viscosity 1 (Pas$^{-1}$) | Viscosity 2 (Pas$^{-1}$) | Viscosity 3 (Pas$^{-1}$) | Yield stress 1 (Pa) | Yield stress 2 (Pa) | Yield stress 3 (Pa) | STABILITY 1 Month at 45° C. |
|----|--------------------------|--------------------------|--------------------------|---------------------|---------------------|---------------------|-----------------------------|
| C1 | 6,402                    | 11,034                   | 10,280                   | 45                  | 95                  | 155                 | Y                           |
| C2 | 1,533                    | 4,043                    | 2,008                    | 15                  | 25                  | 5                   | N                           |
| C3 | 5,373                    | 10,082                   | 10,607                   | 20                  | 100                 | 130                 | Y                           |
| C4 | 3,312                    | 14,535                   | 13,776                   | 20                  | 190                 | 160                 | Y                           |
| C5 | 13,510                   | 21,103                   | 16,355                   | 75                  | 200                 | 160                 | Y                           |
| C6 | 23,200                   | 22,843                   | 18,470                   | 195                 | 185                 | 135                 | Y                           |

Control Cream

The control cream (C1) yields an initial viscosity of about 6,500 Pa s$^{-1}$ with an initial yield stress of 45 Pa. The viscosity and yield stress of the control cream increases with time to about 10,000 Pa s$^{-1}$ and 155 Pa, respectively. This change in rheology with time is due to the delayed hydration of the xanthan gum. The higher the level of xanthan gum, the longer it takes to achieve complete hydration and therefore final formulation equilibrium, as observed in the rheology data.

The Control cream is perceived as stringy with poor skin-feel and rub-out properties.

Comparative Example 2

Hydrophobically treated silicas exhibit both water and oil separation and are particularly unstable, as demonstrated by example C2. Example C2 has a particularly low initial viscosity of 1,533 Pa s$^{-1}$ and a low yield value of 15 Pa indicating a poorly structured, thin and runny product.

Examples C3–C5 of the Invention

These examples are stable at elevated temperatures and produce well structured creams with good skin-feel and rub-in properties.

C3 has an initial viscosity of 5,373 Pa s$^{-1}$ with a yield value of 20 Pa, which increases at 2 weeks to 10,082 Pa s$^{-1}$ and 100 Pa, respectively and from thereon remains constant.

Similarly, example C4 has an initial viscosity of 3,312 Pa s$^{-1}$ with a yield value of 20 Pa, which increases at 2 weeks to 13,776 Pa s$^{-1}$ and 190 Pa, respectively and from thereon remains relatively constant. Example C5 has an improved rheology profile due to the increase in silica thickener loading from 2 to 3%.

Example 6 of the invention

This example is stable at elevated temperature and produces a well structured cream with good skin-feel and rub-in properties. C6 has an initial viscosity of 23,200 Pa s$^{-1}$ with a yield value of 195 Pa which decreases slightly after 1 month to 18,470 Pa s$^{-1}$ and 135 Pa, respectively.

Examples C3 to C6 of the invention are all highly structured, exhibit thixotropy and are stable at elevated temperature. Furthermore, formulations C3 to C6 possess a rich and creamy consistency with improved aesthetic properties, compared to the Control.

All of the thickener systems of the invention deliver a significantly whiter appearance to the cosmetic compositions in which they are incorporated, compared to Veegum.

The silicas used in the present invention are easily dispersed in the water phase of the formulation; are unaffected by high temperatures (about 80° C.) and are not affected by acidic pH.

We claim:

1. Cosmetic composition comprising:
    I) from about 0.01 to 20% by weight of at least one member of the group consisting of $C_1$–$C_{25}$ alpha-hydroxy carboxylic acids and their salts and mixtures thereof;
    ii) from about 0.05 to 0.5% by weight of than gum;
    iii) from about 0.5 to 8% by weight of an amorphous silica;
    iv) a cosmetically acceptable carrier,
    v) wherein the amorphous silica and xantham gum are present in a silica/xanthan gum weight ration from 160:1 to 2:1.

2. Cosmetic composition comprising:
    i) from about 0.01 to 20% by weight of at least one member of the group consisting of $C_1$–$C_{25}$ alpha-hydroxy carboxlylic acids and their salts and mixtures thereof;
    ii) from about 0.05 to 0.5% by weight of xanthan gum;
    iii) from about 0.5 to 8% by weight of an amorphous silica;
    iv) a cosmetically acceptable carrier
wherein the amorphous silica comprises an amorphous silica having a pore size distribution wherein 90% of the pores have a diameter above 15 nanometers, and less than 20% of the pore volume is in pores having a pore diameter between 10 and 30 nanometers, the amorphous silica having a CTAB surface area of less than 100 $m^2$/g.

3. Cosmetic composition according to claim 2 wherein the amorphous silica comprises a fumed silica.

4. Cosmetic composition according to claim 2 or 3 wherein the amorphous silica has a $d_{50}$ within the range of 1 $\mu$m to 8 $\mu$m.

5. A thickened cosmetic composition comprising:
    i) from about 0.01 to 20% by weight of at least one member of the group consisting of $C_1$–$C_{25}$ alpha-hydroxy carboxylic acids and their salts and mixtures thereof;
    ii) from about 0.05 to 0.15% by weight of xanthan gum;
    iii) from about 0.5 to 80% by weight of an amorphous silica;
    iv) a cosmetically acceptable carrier, said composition having a pH within the range of 3 to 5.

6. Cosmetic composition according to claim 1 comprising from 0.1 to 10% by weight of component i), 0.1 to 0.3% by weight of component ii) and 1 to 5% by weight of component iii).

7. Cosmetic composition according to claim 6 wherein the amount of component i) is 3 to 8% by weight of the composition.

8. Cosmetic composition according to claim 1 wherein the weight ratio of silica to xanthan gum is 30:1 to 6.5:1.

9. Cosmetic composition according to claim 4 wherein the $d_{50}$ of the amorphous silica is in the range of 3 $\mu$m to 6 $\mu$m.

10. Cosmetic composition according to claim 1 comprising from 3 to 8% by weight of component i) and less than 0.1% by weight of iii) and the viscosity range of the composition is 8,000 Pa $s^{-1}$ to 30,000 Pa $s^{-1}$.

11. Cosmetic composition according to claim 1 in the form of a cream wherein the carrier is water, the combination of xanthan gum and amorphous silica functioning to provide a thixotropic composition which is stable at acid pH of 3 to 5 and at a temperature of 45° C. and free from syneresis.

12. In a thickened cosmetic composition comprising from about 0.01 to 20% by weight of at least one member of the group consisting of $C_1$–$C_{25}$ alpha hydroxy carboxylic acids, salts thereof and mixtures thereof, together with a thickener and a cosmetically acceptable carrier, the improvement wherein the thickener comprises the combination of from about 0.05 to 0.5% by weight of xanthum gum and from about 0.5 to 8% by weight of an amorphous silica, based on the composition weight: wherein the amorphous silica and xanthan gum are present in a silica/xanthan gum weight ration from 160:1 to 2:1: the composition being characterized by its storage stability at 45° C. and freedom from syneresis.

* * * * *